United States Patent
Braeuer et al.

(10) Patent No.: US 7,229,410 B2
(45) Date of Patent: Jun. 12, 2007

(54) METHOD AND DEVICE FOR DETERMINING A CHARACTERISTIC VALUE FOR THE PERFUSION OF MODIFIED TISSUE REGIONS IN ORGANS OF LIVING BEINGS

(75) Inventors: Kurt Braeuer, Tuebingen (DE); Hans-Martin Haefner, Stuttgrat (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 661 days.

(21) Appl. No.: 10/779,912

(22) Filed: Feb. 17, 2004

(65) Prior Publication Data
US 2004/0220480 A1 Nov. 4, 2004

Related U.S. Application Data

(63) Continuation of application No. PCT/EP02/08855, filed on Aug. 8, 2002.

(30) Foreign Application Priority Data
Aug. 14, 2001 (DE) .............................. 101 40 924.9

(51) Int. Cl.
*A61B 5/00* (2006.01)
*A61B 5/02* (2006.01)
(52) U.S. Cl. ........................................ 600/306; 600/504
(58) Field of Classification Search .................... None
See application file for complete search history.

(56) References Cited
U.S. PATENT DOCUMENTS 4,608,990 A * 9/1986 Elings ........................ 600/317
5,999,843 A * 12/1999 Anbar ........................ 600/474

(Continued)

OTHER PUBLICATIONS

"Cutaneous Blood Flow Measurements for the Detection of Malignancy in Pigmented Skin Lesions", Tur et al., Dermatology 184, 1992, pp. 8-11.

(Continued)

*Primary Examiner*—Robert L. Nasser
(74) *Attorney, Agent, or Firm*—Marshall, Gerstein & Borun LLP (57) ABSTRACT

A method and a device are used for determining a characteristic value for the perfusion of modified, in particular pigmented tissue regions in organs of living beings, for example the skin. By means of a laser flowmeter, a first volumetric flow rate and a second volumetric flow rate of the blood are determined at a first measurement point and at a second measurement point, respectively within the modified tissue region and within the surrounding, unmodified tissue region, in each case as a measurement profile of a volumetric flow rate signal as a function of time. A wavelet analysis of each of the measurement profiles is then carried out as a three-dimensional representation of the signal intensity over a frequency or scaling axis and time. The profile of a vasomotion energy over the frequency or scaling axis is subsequently determined for each of the measurement profiles subjected to the wavelet analysis, the vasomotion energy being the integral of the signal intensity with respect to time for a particular frequency or scaling value. Next, the profile of the vasomotion energy of the second measurement profile is subtracted from the profile of the vasomotion energy of the first measurement profile, so as to form a difference profile. The difference profile is then integrated in order to obtain the characteristic value.

16 Claims, 6 Drawing Sheets

U.S. PATENT DOCUMENTS 6,488,623 B1 * 12/2002 Ozarowski et al. ......... 600/363

OTHER PUBLICATIONS

"Laser Doppler Data Analysis During Interstitial Laser Thermotherapy Under Magnetic Resonance Control. An Experimental Study in Animals", Litscher et al., Biomed. Technik 42, 1997, pp. 93-96.

"Oscillations in the Human Cutaneous Blood Perfusion Signal Modified by Endothelium-Dependent and Endothelium-Independent Vasodilators", Microvascular Research 57, 1999, pp. 298-309.

"Blood Flow Compared in Benign Melanocytic Naevi, Malignant Melanomas and Basal Cell Carcinomas", Clinical and Experimental Dermatology 24, 1999, pp. 107-111.

International Search Report in PCT/EP02/08855 dated Mar. 26, 2003.

International Preliminary Examination Report in PCT/EP02/08855 dated Nov. 14, 2003.

* cited by examiner

METHOD AND DEVICE FOR DETERMINING A CHARACTERISTIC VALUE FOR THE PERFUSION OF MODIFIED TISSUE REGIONS IN ORGANS OF LIVING BEINGS

RELATED APPLICATIONS

This is a continuation of copending International Patent Application PCT/EP02/08855 filed on Aug. 8, 2002 and designating the U.S., which has been published in German as WO 03/015626 A2. and which claims priority of German Patent Application No. 101 40 924 filed on Aug. 14, 2001.

BACKGROUND OF THE INVENTION

1. Field of the Invention

The invention relates to a method for determining a characteristic value for the perfusion of modified tissue regions in organs of living beings.

The invention also relates to a device for determining a characteristic value for the perfusion of modified tissue regions in organs of living beings.

2. Related Prior Art

In dermatology, it is known to use various examination methods, for example direct-light surface microscopy, epi-luminescence microscopy, dermatoscopy etc. in order to examine pigmented tissue regions. These examination methods are based on the discovery that the morphology of different tissue regions, especially the microcirculation inside pigmented tissue regions, can be characterised by characteristic values which can be used as evaluation criteria for this tissue region. In this context, it is known that the capillary vessels are pathologically modified in malignant tumors and so-called hypervascularization is formed in the edge region of the tumorous tissue, with capillary blood vessels growing in the direction of the tumor. This phenomenon is referred to as neoangiogenesis ("in-grown vessels").

It is known to use laser Doppler flowmeters to examine the perfusion in human skin tissue (Kvernmo H. D. et al., Microvascular Research 57, pp. 298–309, 1999). In this context, it is also known to process laser Doppler perfusion signals, which are recorded as a volumetric flow rate as a function of time, specifically by means of a so-called wavelet analysis. The term "wavelet analysis" is intended to mean a method in which a time-variant signal is three-dimensionally represented, specifically over the axes of frequency or scaling, time and signal amplitude. Wavelet analysis is preferably used for those time-variant signals in which a plurality of periodic or quasi-periodic processes are superimposed, possibly together with other stochastic processes. In such a case, wavelet analysis makes it possible to deliberately filter out or deliberately suppress particular frequency or scaling ranges in which individual periodic or quasi-periodic signals occur.

The three-dimensional representation of a laser Doppler perfusion signal by means of wavelet analysis will be referred to below as a "vasomotion field".

In the article by Kvernmo et al. mentioned above, the perfusion in human skin tissue is examined as a function of the administering of particular vasodilating drugs. The characteristic values determined in the scope of that work therefore relate exclusively to the effect of administering these medicaments. Characteristic values which relate to the perfusion behavior of the tissue itself, particularly in comparison between pigmented and nonpigmented tissue regions, are not disclosed in that paper.

SUMMARY OF THE INVENTION

It is an object of the invention to improve a method and device of the type mentioned at the outset, so that it is possible to determine characteristic values which are indeed characteristic of the perfusion of modified, in particular pigmented tissue regions in internal organs, in particular the skin.

In a method of the type mentioned at the outset, this object is achieved according to the invention by the following steps:

a) determining a first volumetric flow rate of the blood by means of laser flowmetry at a first measurement point within the modified tissue region as a first measurement profile of a volumetric flow rate signal as a function of time;

b) determining a second volumetric flow rate of the blood by means of laser flowmetry at a second measurement point within an unmodified tissue region as a second measurement profile of a volumetric flow rate signal as a function of time;

c) carrying out a wavelet analysis of each of the measurement profiles as a three-dimensional representation of the signal intensity over a frequency or scaling axis and time;

d) determining the profile of a vasomotion energy over the frequency or scaling axis for each of the measurement profiles subjected to the wavelet analysis, the vasomotion energy being the integral of the signal intensity with respect to time for a particular frequency or scaling value;

e) subtracting the profile of the vasomotion energy of the second measurement profile from the profile of the vasomotion energy of the first measurement profile, so as to form a first difference profile;

f) integrating the difference profile in order to obtain the characteristic value.

In a preferred variant of the method mentioned at the outset, the object of the invention is furthermore achieved by the following steps:

a) determining a first volumetric flow rate of the blood by means of laser flowmetry at a first measurement point within the modified tissue region as a first measurement profile of a volumetric flow rate signal as a function of time;

b) determining a second volumetric flow rate of the blood by means of laser flowmetry at a second measurement point within an unmodified tissue region as a second measurement profile of a volumetric flow rate signal as a function of time;

c) determining a third volumetric flow rate of the blood by means of laser flowmetry at a third measurement point at the transition between the modified tissue region and the surrounding, unmodified tissue region as a third measurement profile of a volumetric flow rate signal as a function of time;

d) carrying out a wavelet analysis of each of the measurement profiles as a three-dimensional representation of the signal intensity over a frequency or scaling axis and time;

e) determining the profile of a vasomotion energy over the frequency or scaling axis for each of the measurement profiles subjected to the wavelet analysis, the vasomotion energy being the integral of the signal intensity with respect to time for a particular frequency or scaling value;

f) subtracting the profile of the vasomotion energy of the third measurement profile from the profile of the vasomotion energy of the second measurement profile, so as to form a first difference profile;

g) subtracting the profile of the vasomotion energy of the first measurement profile from the profile of the vasomotion energy of the second measurement profile, so as to form a second difference profile;

h) forming an average value of the first and second difference profiles;

j) integrating the average value in order to obtain the characteristic value.

In a device of the type mentioned at the outset, the object of the invention is achieved by the following features:

A device for determining a characteristic value for the perfusion of modified tissue regions in organs of living beings, having:

a) a laser flowmeter for determining
   a first volumetric flow rate of the blood at a first measurement point within the modified tissue region as a first measurement profile of a volumetric flow rate signal as a function of time;
   a second volumetric flow rate of the blood at a second measurement point within an unmodified tissue region as a second measurement profile of a volumetric flow rate signal as a function of time;

b) means for carrying out a wavelet analysis of each of the measurement profiles as a three-dimensional representation of the signal intensity over a scaling axis and time;

c) means for determining the profile of a vasomotion energy over the frequency or scaling axis for each of the measurement profiles subjected to the wavelet analysis, the vasomotion energy being the integral of the signal intensity with respect to time for a particular frequency or scaling value;

d) means for subtracting the profile of the vasomotion energy of the first measurement profile from the profile of the vasomotion energy of the second measurement profile, so as to form a difference profile;

e) means for integrating the difference profile in order to obtain the characteristic value.

In a preferred variant of the device mentioned at the outset, the object of the invention is furthermore achieved by the following features:

A device for determining a characteristic value for the perfusion of modified tissue regions in organs of living beings, having:

a) a laser flowmeter for determining
   a first volumetric flow rate of the blood at a first measurement point within-the modified tissue region as a first measurement profile of a volumetric flow rate signal as a function of time;
   a second volumetric flow rate of the blood at a second measurement point within an unmodified tissue region as a second measurement profile of a volumetric flow rate signal as a function of time;
a third volumetric flow rate of the blood at a third measurement point at the transition between the modified tissue region and the surrounding, unmodified tissue region as a third measurement profile of a volumetric flow rate signal as a function of time;

b) means for carrying out a wavelet analysis of each of the measurement profiles as a three-dimensional representation of the signal intensity over a frequency or scaling axis and time;

c) means for determining the profile of a vasomotion energy over the frequency or scaling axis for each of the measurement profiles subjected to the wavelet analysis, the vasomotion energy being the integral of the signal intensity with respect to time for a particular frequency or scaling value;

d) means for subtracting the profile of the vasomotion energy of the third measurement profile from the profile of the vasomotion energy of the second measurement profile, so as to form a first difference profile;

e) means for subtracting the profile of the vasomotion energy of the first measurement profile from the profile of the vasomotion energy of the second measurement profile, so as to form a second difference profile;

f) means for forming-an-average value of the first and second difference profiles;

g) means for integrating the average value in order to obtain the characteristic value.

The object underlying the invention is fully achieved in this way.

In fact, it has been found that the features listed above make it possible to determine characteristic values which permit virtually 100% determination of the properties of the modified tissue region being examined. This reliability has also been confirmed in a clinical study.

According to a further object, the characteristic value may be compared with a reference value.

This measure has the advantage that it is possible to assign the characteristic value which is determined to clinically determined limit values, so as to draw conclusions therefrom in order to describe the state of the modified tissue region.

Other advantages can be found in the description and the appended drawing.

It is to be understood that the features mentioned above, and those which will be mentioned below, may be used not only in the respectively indicated combination but also in other combinations or individually, without departing from the scope of the present invention.

BRIEF DESCRIPTION OF THE DRAWINGS

An embodiment of the invention is represented in the drawing and will be explained in more detail in the description below.

DESCRIPTION OF A PREFERRED EMBODIMENT

Figure 1:
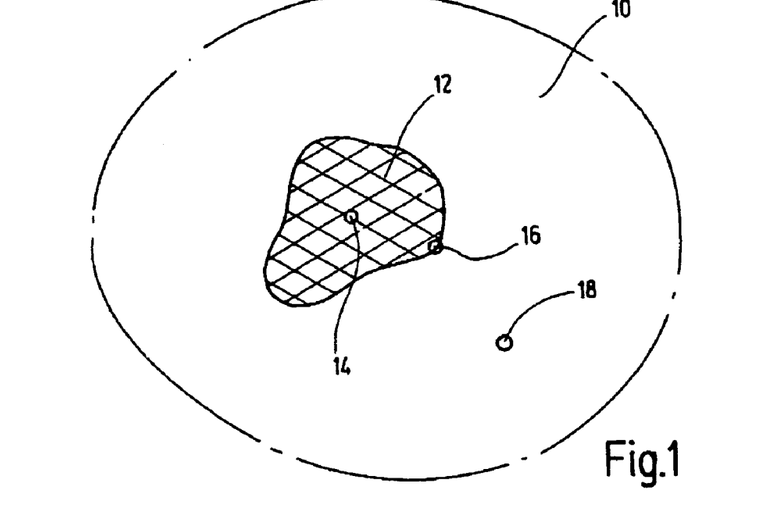
FIG. 1 shows a highly schematized representation of a skin region, in which there is a pigmented tissue region, while specifying measurement points selected according to the invention.

In FIG. 1, 10 denotes a skin region of a human in a highly schematized way. Within the skin region 10, there is a modified tissue region 12, which is a pigmented tissue region in the exemplary case being represented. The pigmented tissue region 12 may be benign or malignant. Benign manifestations include freckles, liver spots and the like (melanocytic nevi), while malignant manifestations include the various types of skin cancer (melanomas). The skin region 10 stands for an example of any organ of a living being, particularly an internal organ.

In FIG. 1, 14 denotes a first measurement point at the centre of the pigmented tissue region 12, 16 denotes a second measurement point at the edge of the pigmented tissue region 12, and 18 denotes a third measurement point in the surrounding, nonpigmented tissue region. The second measurement point 16 is not absolutely necessary for carrying out the method, although it is evaluated in preferred variants of the method.

At the two measurement points 14, 18, or the three measurement points 14, 16 and 18, measurements are then carried out by means of a laser Doppler flowmeter. Such laser Doppler flowmeters are known to the person skilled in the art, and are sold for example under the device reference "Periflux System 5000" by Perimed, Stockholm, Sweden.

In laser Doppler flowmeters, a laser beam is guided into the vessels to be examined. Owing to the Doppler effect, the light reflected by the moving blood corpuscles has its frequency, i.e. color, shifted as well as its intensity. In this way, it is possible to carry out measurements of the volumetric flow rate of the blood. Measurement profiles of a volumetric flow rate signal as a function of time are then obtained.

Figure 2A:
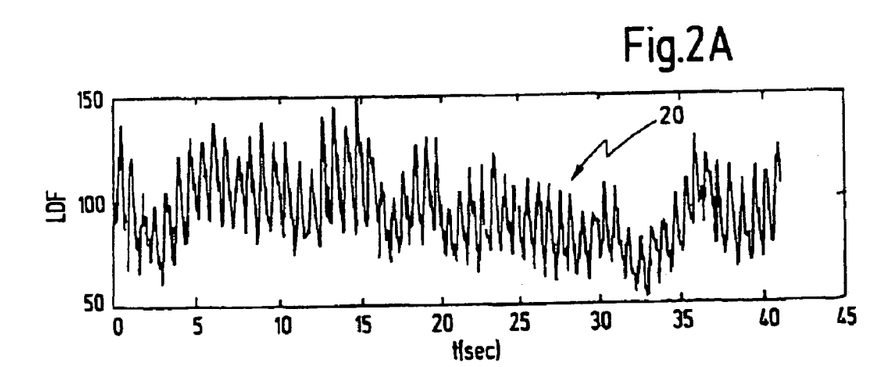
FIGS. 2A and 2B show laser Doppler perfusion signals, as can be deter-mined at the measurement points according to FIG. 1 as volumetric flow rates of the blood as a function of time.
Figure 2B:
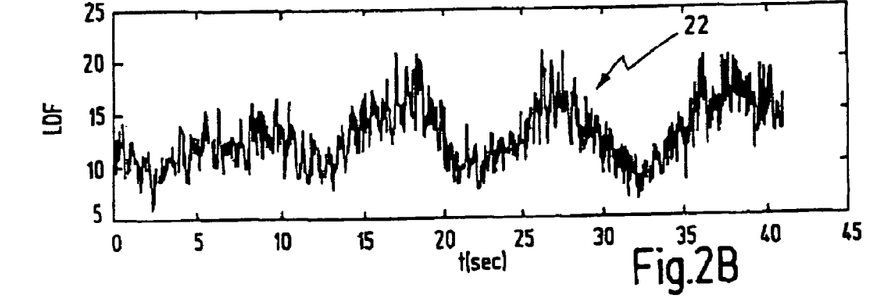

FIGS. 2A and 2B represent two such measurement profiles 20 and 22 for the measurement points 14 and 18 in FIG. 1. It can be seen clearly that a larger signal amplitude is obtained at the first measurement point 14 and a smaller signal amplitude is obtained at the third measurement point 18. The measurement profiles 20 and 22 also reveal that a plurality of periodic and quasi-periodic processes seem to be superimposed on a stochastic process. The periodic or quasi-periodic processes are in this case the vital physiological functions of the human body (respiration, pulse etc.). These processes change in a known way with time, so that the measurement profiles according to FIGS. 2A and 2B per se are not very informative. It can, however, be inferred therefrom that the pigmented tissue region 12 seems to be perfused substantially more than the surrounding nonpigmented tissue region.

In order to make the recorded measurement profiles 20 and 22 more informative, a special wavelet analysis is carried out according to the invention. As already mentioned above, wavelet analysis is a tool known per se in signal processing to convert a time profile into a three-dimensional representation with the axes of time, frequency or scaling and signal intensity, for measurement profiles of the type available here. From the wavelet analysis representation, the various periodic, quasiperiodic and stochastic processes can then be identified better and, if need be, filtered out or suppressed.

FIGS. 3A to 3D present four such representations, the abscissa being the time axis t and the ordinate being the frequency or scaling axis s. The third axis of signal intensity is produced in the representations of FIGS. 3A to 3D by differential darkening (or coloring).

Figure 3A:
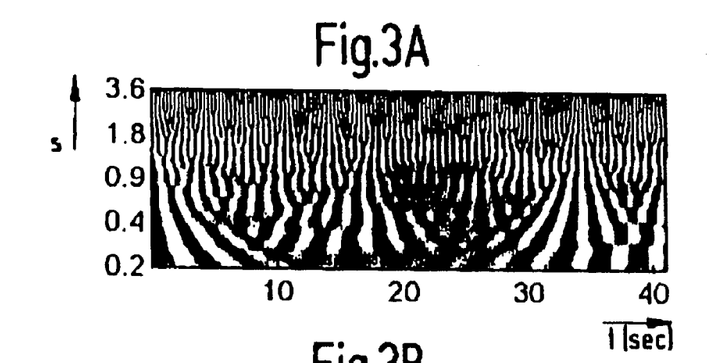
FIGS. 3A to 3D show four vasomotion fields, as are obtained by wavelet analysis from laser Doppler perfusion signals.
Figure 3B:
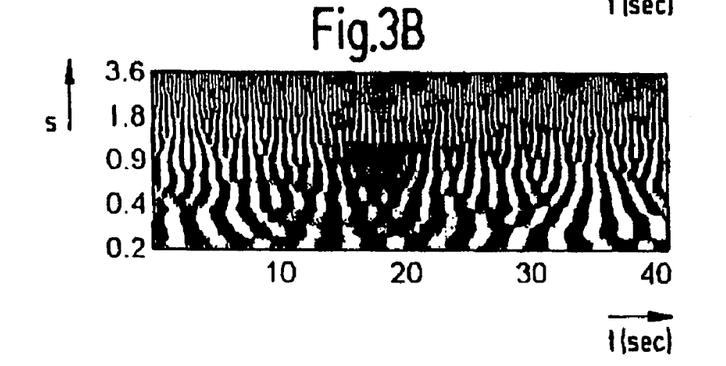
Figure 3C:
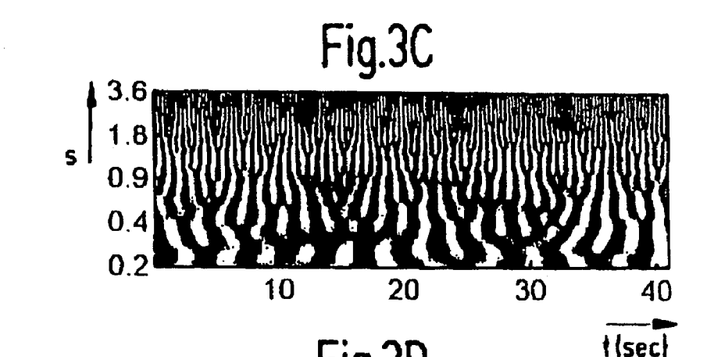
Figure 3D:
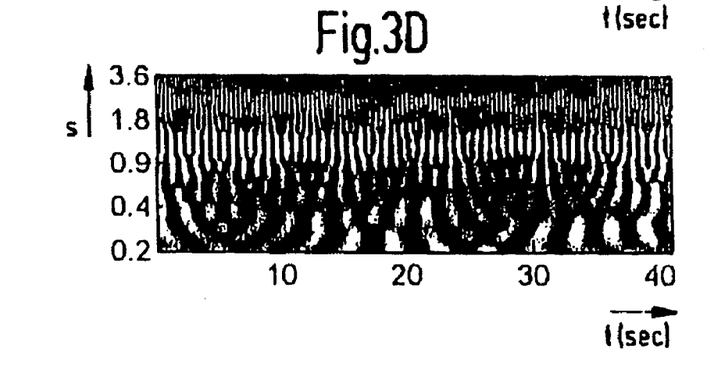

The representation in FIG. 3A corresponds to a reference pattern for benign tissue, the representation in FIG. 3B corresponds to a central measurement for benign tissue, while FIGS. 3C and 3D represent the corresponding reference and central measurements for malignant tissue.

Figure 4:
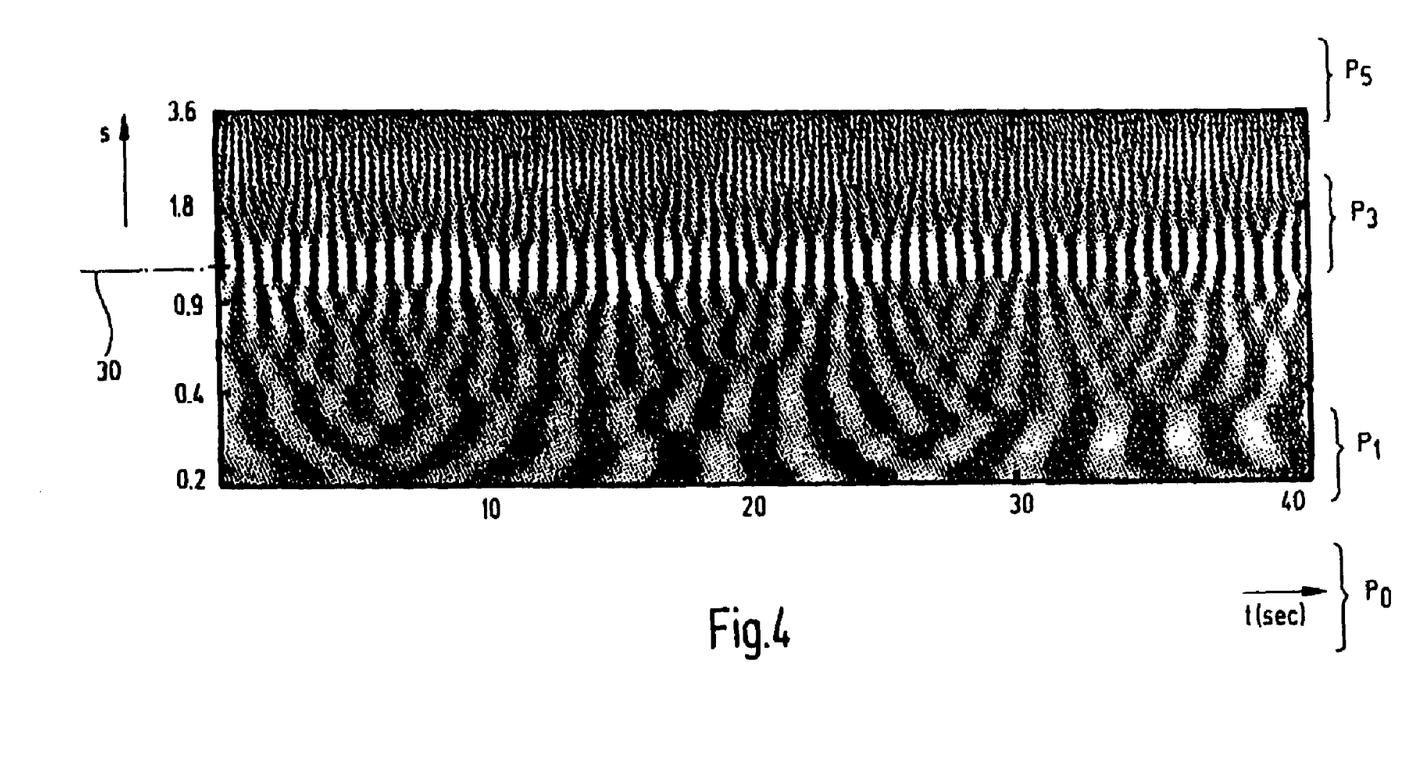
FIG. 4 shows the vasomotion field according to FIG. 3D, on an enlarged scale and in order to explain further details.

For further explanation, the representation of FIG. 3D is shown again on an enlarged scale in FIG. 4. The right-hand half of FIG. 4 represents four typical regions $p_0$, $p_1$, $p_3$ and $p_5$. The region $p_0$, which is not in fact shown in the actual image, corresponds to the respiration (slow frequency), which merges through a transition region $p_1$ into the region $p_3$ of the heartbeat (medium frequency), which is followed further above after another transition region by the region $p_5$ of the reflected pulse waves (high frequency).

This provides a characteristic pattern with periodic bands, which are assigned to the respective periodic processes.

In order to interpret this wavelet analysis, so-called scaling levels are defined on the frequency or scaling axis s, one of which is indicated in FIG. 4 by 30 in the region $p_3$ of the heartbeat. By progressing along the scaling level 30 in the abscissa direction through the diagram according to FIG. 4 and integrating the (preferably squared) signal values with respect to the time axis, then a value is obtained for each scaling level 30 which will be referred to below as a "vasomotion energy E". The vasomotion energy E can be plotted for the various scaling levels s, as is done in FIGS. 5 and 6.

Figure 5:
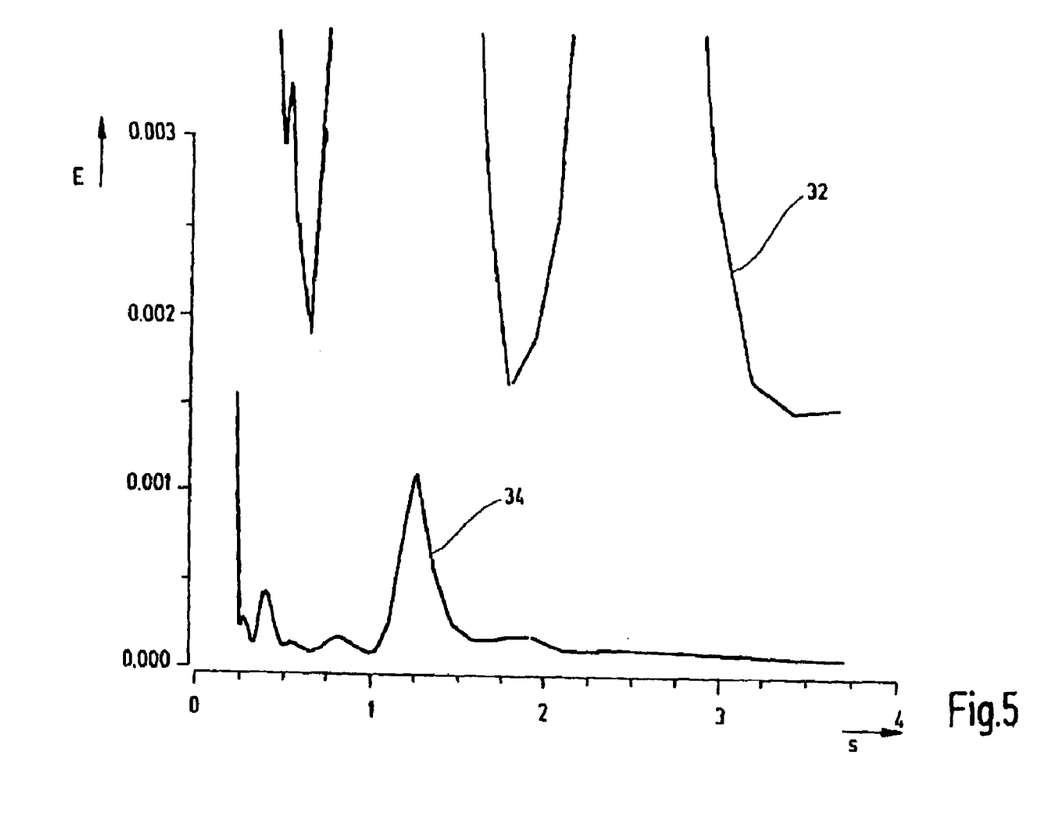
FIG. 5 shows the graphical profile of the vasomotion energy over a scaling axis for a malignant pigmented tissue region, in comparison with the surrounding tissue.

In FIG. 5, a first profile denoted 32 and a second profile denoted 34 of the vasomotion energy E are plotted against the scaling level (or frequency axis) s. The first profile 32 belongs to a malignant melanoma (for example corresponding to the wavelet analysis according to FIG. 3D, i.e. according to FIG. 4), while the second profile 34 corresponds to the surrounding nonpigmented skin region. It can be seen clearly that there is a significant difference between the profiles 32 and 34.

Figure 6:
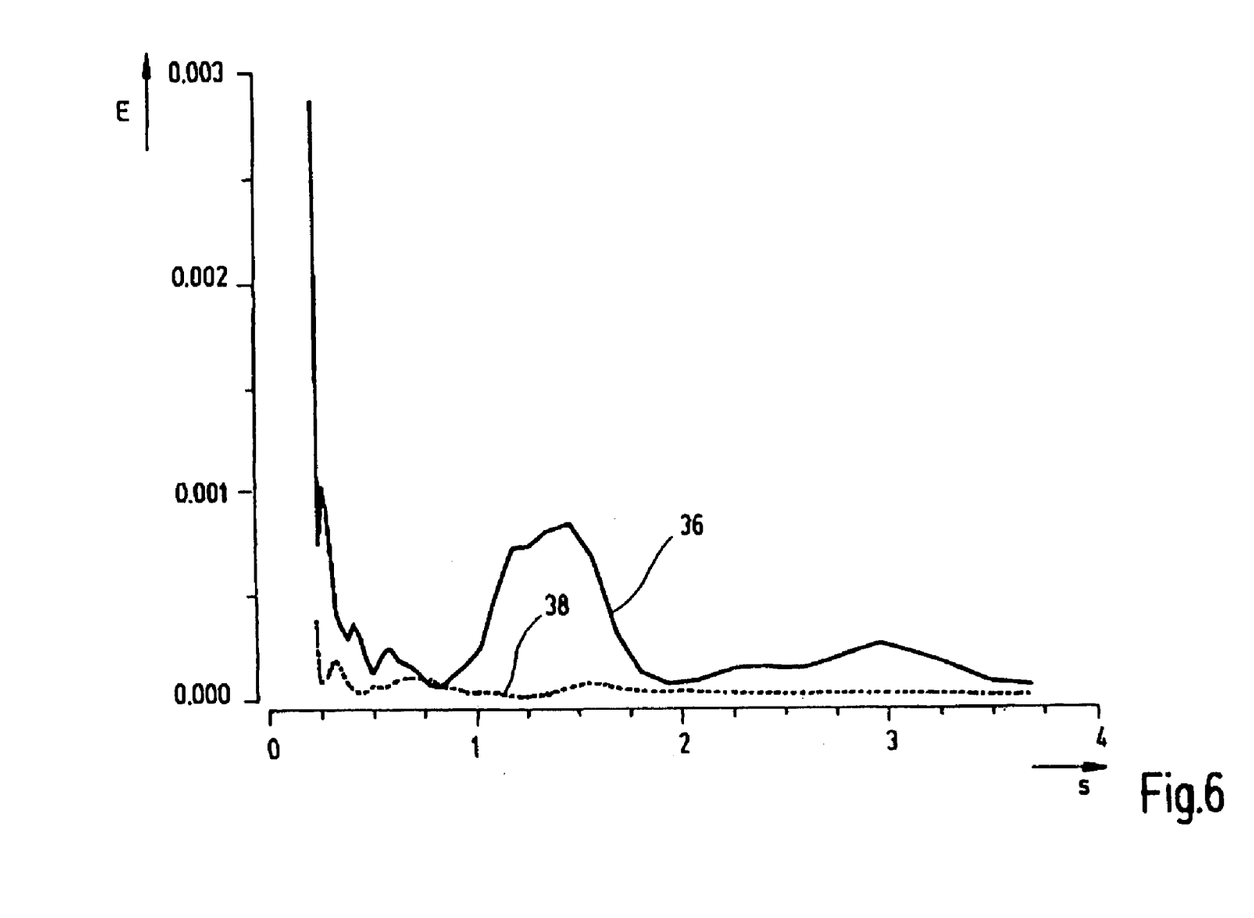
FIG. 6 shows a representation similar to FIG. 5, but for a benign pigmented tissue region.

For comparison, FIG. 6 shows corresponding profiles which were obtained from the examination of likewise pigmented but benign tissue regions in comparison with the surrounding nonpigmented tissue. A third profile 38 corresponds to the nonpigmented surrounding region in this case, while the fourth profile 36 corresponds to a melanocytic nevus. Apart from the region between s=1 and s=2, the profiles are not so significantly different as in the case of FIG. 5.

In order to explain how a reliable characteristic value can be determined from such measurements, reference will again be made to the representations according to FIGS. 2A and 2B in conjunction with FIG. 1.

According to a first variant of the invention, the profile of the vasomotion energy E corresponding to the second measurement profile 22 (surrounding nonpigmented tissue) is now subtracted from the profile of the vasomotion energy E of the first measurement profile 24 (centre of the pigmented region 12).

The difference profile obtained in this way is then integrated. This integral is the intended characteristic value, which will be referred to below as ΔE.

According to a second variant of the invention, however, the profile of the vasomotion energy E corresponding to the second measurement profile 22 (edge region) is subtracted from the profile of the vasomotion energy E of the third measurement profile 24 (surrounding nonpigmented tissue), and the profile of the vasomotion energy E of the first measurement profile 20 (centre of the pigmented region 12) is likewise subtracted from the profile of the vasomotion energy E, also of the third measurement profile 24.

The average value is then formed from the difference profiles obtained in this way, and this average value is integrated. This integral is the intended characteristic value, which will be referred to below as ΔE.

Figure 7:
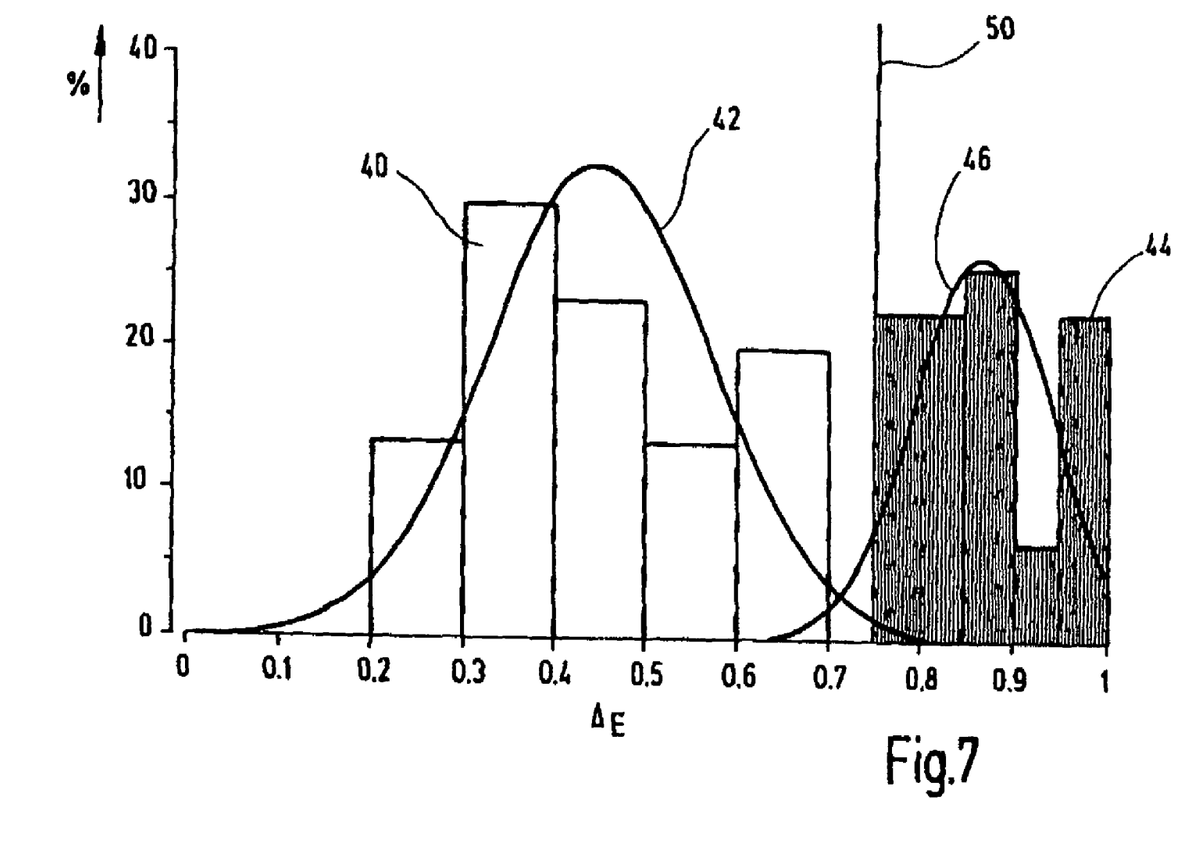
FIG. 7 shows a bar chart to explain a clinical study carried out according to the invention.

FIG. 7 represents the result of a clinical study, which was carried out on 61 patients. Measurements corresponding to the representations in FIGS. 1 and 2 were carried out on these patients, and these measurements were then evaluated in the way described above. When determining the characteristic value ΔE, they were normalized to a range of between 0 and 1 for better clarity.

After the measurements, samples were taken from the patients in the respective pigmented tissue regions 12, and these were histologically examined.

In FIG. 7, the bars 40 show the results of those patients for whom benign manifestations of the pigmented tissue region were found in the course of the histological examination. For example, about 30% of these patients had a characteristic value ΔE of between 0.3 and 0.4. From the bars 40, it was possible to determine a first distribution curve 42 for these patients having benign pigmented tissue regions.

The bars 44 represented as dark in FIG. 7, however, belong to those patients for whom malignant pigmented tissue regions were established subsequently in the histological examination. From the bars 44, it was possible to derive a second distribution curve 46 for these patients.

As can be seen clearly from FIG. 7, the two distribution curves 42 and 46 are separated relatively distinctly from each other on the ΔE axis. It is therefore possible to specify a limit value 50 which, with the selected normalization to values of between 0 and 1, lies at ΔE=0.75.

In the scope of the present invention, the wavelet analysis is preferably carried out by using the following concepts:

The measurement profiles 20 and 22 according to FIGS. 2A and 2B can be analytically described as follows:

$$\xi(t_n), t_n = \frac{n-1}{f_{samp}}, n \in [1, N],$$

where $\xi(t_n)$ represents the measurement points at the times $t_n$, and a constant sampling rate $f_{samp}$ was selected. The vasomotion field V at the time $t_\tau$ on a scaling level s is then obtained from the wavelet representation of the time profile as:

$$V(t_\tau, s) = \sum_{n \in \{1...N\}} \phi_s(t_n - t_\tau)\xi(t_n).$$

The wavelets $\phi_s$ are derived from a so-called mother wavelet $\phi$. For analysis of the vasomotion data in the scope of the present invention, the following mother wavelet was found to be particularly suitable:

$$\phi(t) = \cos(17.3932 \cdot t)e^{-t^2}.$$

This mother wavelet describes a local oscillation over about ten periods. The wavelets are derived from the mother wavelet $\phi$ in the following way:

$$\phi_s(t) = \sqrt{s}\phi(st).$$

$\sqrt{s}$ normalizes the wavelets $\phi_s$ independently of the scaling level s.

The scaling levels are subdivided into so-called "octaves" and "voices":

$$s \rightarrow s_\sigma = 2^{\sigma/N^{(voices)}} mit\ \sigma \in \{0 \ldots N^{(voices)}N^{(octaves)}\}.$$

$N^{(octaves)}$ is the number of octaves in the vasomotion field, and $N^{(voices)}$ is the number of voices per octave. This leads to the so-called continuous wavelet transformation.

The voices and octaves of the scaling levels are closely related to the frequencies of the Fourier spectrum. For better understanding, the scaling values are indicated in units which are as close as possible to the Fourier frequencies. Five different scaling ranges are then obtained, as already explained above with reference to FIG. 4:

P0: $s_\sigma$=0.15–0.31 (respiration);
P1: $s_\sigma$=0.31–0.62 (transition from respiration to heartbeat);
P2: $s_\sigma$=0.62–1.20 (transition from respiration to heartbeat);
P3: $s_\sigma$=1.20–2.50 (heartbeat);
P4: $s_\sigma$=2.50–5.00 (transition-from heartbeat to reflected pulse waves);
P5: $s_\sigma$=5.00–10.00 (reflected pulse waves).

Overall, the vasomotion field V is then given as:

$$V_{\tau s_\sigma} = \sum_{n \in \{1...N\}} \phi_{s_\sigma}(t_n - t_\tau)\xi(t_n).$$

Such vasomotion fields V are represented as two-dimensional printouts with gray-value- or color-coded amplitudes in FIGS. 3A to 3D and 4.

For further evaluation of the signals, the vasomotion field energy $E_{s_\sigma}$ is determined for each scaling level $s_\sigma$ by summation over the time τ.

$$E_{s_\tau} = \sum_{\tau \in N} V_{\tau s_\sigma}^2.$$

For comparison of the different vasomotion fields V, in particular between healthy and pigmented tissue, the energy difference or characteristic value ΔE is determined as follows:

$$\Delta E = C^{-1} \sum_{s,\sigma} |E_{s_\sigma}^{(healthy)} - E_{s_\sigma}^{(pigmented)}|,$$

$$C = \sum_{s,\sigma} |E_{s_\sigma}^{(healthy)} - E_{s_\sigma}^{(pigmented)}| \Rightarrow \Delta E \in [0, 1].$$

What is claimed, is:

1. A method for determining a characteristic value for the perfusion of modified tissue regions in organs of living beings, having the following steps:
 a) determining a first volumetric flow rate of the blood by means of laser flowmetry at a first measurement point within the modified tissue region as a first measurement profile of a volumetric flow rate signal as a function of time;
 b) determining a second volumetric flow rate of the blood by means of laser flowmetry at a second measurement point within an unmodified tissue region as a second measurement profile of a volumetric flow rate signal as a function of time;
 c) carrying out a wavelet analysis of each of the measurement profiles as a three-dimensional representation of the signal intensity over a frequency or scaling axis and time;
 d) determining the profile of a vasomotion energy over the frequency or scaling axis for each of the measurement profiles subjected to the wavelet analysis, the vasomotion energy being the integral of the signal intensity with respect to time for a particular frequency or scaling value;

e) subtracting the profile of the vasomotion energy of the second measurement profile from the profile of the vasomotion energy of the first measurement profile, so as to form a first difference profile;

f) integrating the difference profile in order to obtain the characteristic value.

2. The method of claim 1, wherein the characteristic value is compared with a reference value.

3. The method of claim 1, wherein the first measurement point is located in a pigmented tissue region.

4. The method of claim 1, wherein the tissue regions are regions of the skin of the living being.

5. A method for determining a characteristic value for the perfusion of modified tissue regions in organs of living beings, having the following steps:

a) determining a first volumetric flow rate of the blood by means of laser flowmetry at a first measurement point within the modified tissue region as a first measurement profile of a volumetric flow rate signal as a function of time;

b) determining a second volumetric flow rate of the blood by means of laser flowmetry at a second measurement point within an unmodified tissue region as a second measurement profile of a volumetric flow rate signal as a function of time;

c) determining a third volumetric flow rate of the blood by means of laser flowmetry at a third measurement point at the transition between the modified tissue region and the surrounding, unmodified tissue region as a third measurement profile of a volumetric flow rate signal as a function of time;

d) carrying out a wavelet analysis of each of the measurement profiles as a three-dimensional representation of the signal intensity over a frequency or scaling axis and time;

e) determining the profile of a vasomotion energy over the frequency or scaling axis for each of the measurement profiles subjected to the wavelet analysis, the vasomotion energy being the integral of the signal intensity with respect to time for a particular frequency or scaling value;

f) subtracting the profile of the vasomotion energy of the third measurement profile from the profile of the vasomotion energy of the second measurement profile, so as to form a first difference profile;

g) subtracting the profile of the vasomotion energy of the first measurement profile from the profile of the vasomotion energy of the second measurement profile, so as to form a second difference profile;

h) forming an average value of the first and second difference profiles;

i) integrating the average value in order to obtain the characteristic value.

6. The method of claim 5, wherein the characteristic value is compared with a reference value.

7. The method of claim 5, wherein the first measurement point is located in a pigmented tissue region.

8. The method of claim 5, wherein the tissue regions are regions of the skin of the living being.

9. A device for determining a characteristic value for the perfusion of modified tissue regions in organs of living beings, having:

a) a laser flowmeter for determining
a first volumetric flow rate of the blood at a first measurement point within the modified tissue region as a first measurement profile of a volumetric flow rate signal as a function of time;
a second volumetric flow rate of the blood at a second measurement point within an unmodified tissue region as a second measurement profile of a volumetric flow rate signal as a function of time;

b) means for carrying out a wavelet analysis of each of the measurement profiles as a three-dimensional representation of the signal intensity over a scaling axis and time;

c) means for determining the profile of a vasomotion energy over the frequency or scaling axis for each of the measurement profiles subjected to the wavelet analysis, the vasomotion energy being the integral of the signal intensity with respect to time for a particular frequency or scaling value;

d) means for subtracting the profile of the vasomotion energy of the first measurement profile from the profile of the vasomotion energy of the second measurement profile, so as to form a first difference profile;

e) means for integrating the difference profile in order to obtain the characteristic value.

10. The device of claim 9, having means for comparing the characteristic value with a reference value.

11. The device of claim 9, wherein the first measurement point is located in the pigmented tissue region.

12. The device of claim 9, wherein the tissue regions are regions of the skin of the living being.

13. A device for determining a characteristic value for the perfusion of modified tissue regions in organs of living beings, having:

a) a laser flowmeter for determining
a first volumetric flow rate of the blood at a first measurement point within the modified tissue region as a first measurement profile of a volumetric flow rate signal as a function of time;
a second volumetric flow rate of the blood at a second measurement point within an unmodified tissue region as a second measurement profile of a volumetric flow rate signal as a function of time;
a third volumetric flow rate of the blood at a third measurement point at the transition between the modified tissue region and the surrounding, unmodified tissue region as a third measurement profile of a volumetric flow rate signal as a function of time;

b) means for carrying out a wavelet analysis of each of the measurement profiles as a three-dimensional representation of the signal intensity over a frequency or scaling axis and time;

c) means for determining the profile of a vasomotion energy over the frequency or scaling axis for each of the measurement profiles subjected to the wavelet analysis, the vasomotion energy being the integral of the signal intensity with respect to time for a particular frequency or scaling value;

d) means for subtracting the profile of the vasomotion energy of the third measurement profile from the profile of the vasomotion energy of the second measurement profile, so as to form a first difference profile;

e) means for subtracting the profile of the vasomotion energy of the first measurement profile from the profile of the vasomotion energy of the second measurement profile, so as to form a second difference profile;

f) means for forming an average value of the first and second difference profiles;

g) means for integrating the average value in order to obtain the characteristic value.

14. The device of claim 13, having means for comparing the characteristic value with a reference value.

15. The device of claim 13, wherein the first measurement point is located in the pigmented tissue region.

16. The device of claim 13, wherein the tissue regions are regions of the skin of the living being.

* * * * *